United States Patent
Elachchabi et al.

(10) Patent No.: US 9,271,734 B2
(45) Date of Patent: Mar. 1, 2016

(54) METHODS AND DEVICES FOR SHEATH COMPRESSION

(71) Applicant: Covidien LP, Mansfield, MA (US)

(72) Inventors: Amin Elachchabi, Hamden, CT (US); Joshua Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/893,760

(22) Filed: May 14, 2013

(65) Prior Publication Data

US 2013/0253549 A1 Sep. 26, 2013

Related U.S. Application Data

(62) Division of application No. 12/557,042, filed on Sep. 10, 2009, now abandoned.

(60) Provisional application No. 61/099,015, filed on May 14, 2013.

(51) Int. Cl.
*A61B 17/11* (2006.01)

(52) U.S. Cl.
CPC ............. *A61B 17/11* (2013.01); *A61B 17/1114* (2013.01); *A61B 2017/1103* (2013.01); *A61B 2017/1107* (2013.01)

(58) Field of Classification Search
CPC ........... A61B 17/11; A61B 2017/1103; A61B 2017/1107; A61B 17/1114; A61B 2017/1117; A61B 2017/1121; A61B 2017/1125; A61B 2017/1142
USPC ............... 606/151–155, 200, 213, 1.23, 1.28, 606/1.29, 131.13
See application file for complete search history.

(56) References Cited

U.S. PATENT DOCUMENTS

| | | | |
|---|---|---|---|
| 1,470,707 A | 10/1922 | Bates | |
| 3,155,095 A | 11/1964 | Brown | |
| 3,254,651 A | 6/1966 | Collito | |
| 3,620,218 A | 11/1971 | Schmitt et al. | |
| 3,945,052 A | 3/1976 | Liebig | |
| 4,182,339 A | 1/1980 | Hardy | |
| 4,190,909 A | 3/1980 | Ablaza | |
| 4,719,916 A | 1/1988 | Ravo | |
| 5,151,105 A | 9/1992 | Kwan-Gett | |
| 5,254,113 A | 10/1993 | Wilk | |
| 5,290,305 A | 3/1994 | Inoue | |
| 5,425,739 A | 6/1995 | Jessen | |
| 5,972,017 A * | 10/1999 | Berg et al. | 606/198 |
| 6,013,854 A | 1/2000 | Moriuchi | |

(Continued)

FOREIGN PATENT DOCUMENTS

| | | |
|---|---|---|
| EP | 0 824 901 | 2/1998 |
| EP | 1 655 001 | 5/2006 |

(Continued)

OTHER PUBLICATIONS

European Search Report for EP 09252247.3-2310 date of completion Jan. 8, 2010 (3 pgs.).

*Primary Examiner* — Jing Ou

(57) ABSTRACT

A sheath is configured for elongation from a first length to a second, longer length and a retention member retains the sheath at the first length. A portion of the retention member is removed or disengaged, the sheath is released and expands in situ to the second longer length. A method for releasing the retention member is also disclosed.

1 Claim, 3 Drawing Sheets

(56) References Cited

U.S. PATENT DOCUMENTS

| | | |
|---|---|---|
| 6,152,956 A | 11/2000 | Pierce |
| 6,358,275 B1 | 3/2002 | McIlroy et al. |
| 6,613,072 B2 | 9/2003 | Lau et al. |
| 6,926,724 B1 | 8/2005 | Chu |
| 7,771,382 B2 | 8/2010 | Levine et al. |
| 8,128,684 B2 | 3/2012 | Lauterjung |
| 2003/0050664 A1 | 3/2003 | Solem |
| 2003/0130721 A1 | 7/2003 | Martin et al. |
| 2003/0135267 A1* | 7/2003 | Solem et al. ............... 623/1.18 |
| 2004/0098091 A1* | 5/2004 | Erbel et al. ................. 623/1.13 |
| 2004/0138734 A1 | 7/2004 | Chobotov et al. |
| 2004/0168691 A1 | 9/2004 | Sharkawy et al. |
| 2005/0033448 A1 | 2/2005 | Lee |
| 2005/0038502 A1 | 2/2005 | Waysbeyn et al. |
| 2005/0080483 A1* | 4/2005 | Solem et al. ............... 623/2.11 |
| 2005/0096750 A1 | 5/2005 | Kagan et al. |
| 2005/0171599 A1 | 8/2005 | White |
| 2005/0182484 A1 | 8/2005 | Patel |
| 2005/0228409 A1 | 10/2005 | Coppi |
| 2005/0251180 A1 | 11/2005 | Burton et al. |
| 2005/0273060 A1 | 12/2005 | Levy et al. |
| 2006/0212126 A1 | 9/2006 | Zucker |
| 2006/0265082 A1 | 11/2006 | Meade et al. |
| 2006/0271104 A1* | 11/2006 | Viola et al. ................. 606/214 |
| 2007/0010865 A1 | 1/2007 | Dann et al. |
| 2007/0043425 A1 | 2/2007 | Hartley et al. |
| 2007/0083271 A1 | 4/2007 | Levine et al. |
| 2007/0118157 A1* | 5/2007 | Zuidema et al. ............ 606/153 |
| 2007/0173868 A1 | 7/2007 | Bachinski et al. |
| 2007/0173924 A1* | 7/2007 | Gelbart et al. .............. 623/1.15 |
| 2007/0233162 A1 | 10/2007 | Gannoe et al. |
| 2008/0009889 A1 | 1/2008 | Pokorney et al. |
| 2008/0039878 A1 | 2/2008 | Williams et al. |
| 2008/0294234 A1 | 11/2008 | Hartley et al. |
| 2010/0010517 A1 | 1/2010 | Stopek et al. |
| 2010/0010518 A1 | 1/2010 | Stopek et al. |
| 2010/0010519 A1 | 1/2010 | Stopek et al. |
| 2010/0030321 A1 | 2/2010 | Mach |

FOREIGN PATENT DOCUMENTS

| | | |
|---|---|---|
| EP | 1 702 571 | 9/2006 |
| EP | 1 836 974 | 9/2007 |
| EP | 1 839 624 | 10/2007 |
| WO | WO 97/31590 | 9/1997 |
| WO | WO 01/21102 | 3/2001 |
| WO | WO 2004/086984 | 10/2004 |
| WO | WO 2005/037073 | 4/2005 |
| WO | WO 2005/094525 | 10/2005 |
| WO | WO 2005/110280 | 11/2005 |
| WO | WO 2009/046998 | 4/2009 |

* cited by examiner

METHODS AND DEVICES FOR SHEATH COMPRESSION

CROSS REFERENCE TO RELATED APPLICATIONS

This application is a divisional of U.S. patent application Ser. No. 12/557,042, filed Sep. 10, 2009, now abandoned, which claims priority to, and the benefit of, U.S. Provisional Patent Application Ser. No. 61/099,015, filed Sep. 22, 2008. U.S. patent application Ser. No. 12/486,333, filed Jun. 17, 2009, issued as U.S. Pat. No. 8,491,612, which claims priority to U.S. Provisional Patent Application Ser. No. 61/079,198, filed Jul. 9, 2008; U.S. patent application Ser. No. 12/486,346 filed Jun. 17, 2009, now abandoned, which claims priority to U.S. Provisional Patent Application Ser. No. 61/079,200, filed Jul. 9, 2008; U.S. patent application Ser. No. 12/486,352 filed Jun. 17, 2009, which claims priority to U.S. Provisional Patent Application Ser. No. 61/079,202, filed Jul. 9, 2008, the entire content of which are incorporated herein by reference.

TECHNICAL FIELD

The present disclosure relates to a sheath for use with an anastomosis, and more particularly to sheaths in a compressed position for delivery to a surgical site.

BACKGROUND

An anastomosis, or the joining of two vessels, such as esophagus, colon, or other parts of the digestive tract, is a common procedure. Sheaths may be placed over the anastomotic site to protect the anastomotic site during healing.

Specific patient populations such as patients with diabetes T1, T2, or other immuno-compromised patients {such as chemotherapy patients) are more prone to anastomotic leaks. These patient populations have longer healing profiles and sometimes weaker immune systems and these factors may lead to an increase in leak occurrence. Unfortunately, in most cases, anastomotic leaks are not detected until clinical symptoms present themselves.

Copending, commonly assigned patent applications 61/079,198, 61/079,200, and 61/079,202 disclose various embodiments of sheaths which may assist in decreasing leaks and the risks associated with anastomotic leaks. However, it would be advantageous to retain the sheath in a compressed position at least for insertion.

SUMMARY

Medical devices, and more particularly sheaths are described herein which provide for protection of an anastomosis and more particularly sheaths which are provided in a compressed position for at least insertion. The sheath is configured for elongation in situ from a first length to a second, longer length; the sheath is provided in combination with a retention member, the retention members retaining the sheath at the first length. In some embodiments, upon disengagement of at least a portion of the retention member from the sheath, the sheath is capable of elongation longitudinally from the first length to the second, longer length. In other embodiments, upon removal of at least a portion of the retention member, the sheath extends to the second, longer length. Alternatively, upon severing of the retention member, the sheath may elongate from the first length to the second, longer length.

In one alternate embodiment, a sheath includes a distal portion and a proximal portion, and the sheath is retained in a first position having a first length for insertion into a body lumen and is elongated to a second position having a second greater length for placement in a body lumen, the distal portion of the sheath longitudinally extending past an anastomotic site. Furthermore, the sheath may be retained in the first position by a retention member.

Retention members of the present disclosure are selected from the group consisting of fibers, sutures, clips, pins, and staples. The retention members may also be glues or adhesives. The retention member may penetrate at least a portion of the sleeve. Materials which may be used to make the retention member include materials selected from the group consisting of polysaccharides, proteins, vinyl polymers, PEG-based polymers, and combinations thereof. The retention member may also be water soluble. In some embodiments, the retention member may be in the form of a polymer coating. In other embodiments, the retention member encapsulates the sheath.

A method of treating a patient is also disclosed, the method including the steps of providing a sheath having a distal end and a proximal end, the sheath configured for elongation in situ from first length to a second, longer length, and a retention member; attaching the proximal end of the sheath to a body lumen at a region proximal of an anastomosis; and, releasing the retention member so the sheath is extendable to the second length. The method may further include the step of grasping the sheath and applying a force to extend the sheath distally past an anastomotic site.

BRIEF DESCRIPTION OF THE DRAWINGS

Various preferred embodiments of the medical devices are described herein with reference to the drawings, in which.

DETAILED DESCRIPTION OF EMBODIMENTS

The present disclosure is directed to a retention member which retains an anastomotic sheath at a first length for insertion into a body lumen, and upon disengagement or release of the retention member, the sheath may elongate in situ to a second, longer length. The term "sheath" as used herein includes a medical device defining a passage, which allows for the transport and flow of fluids therethrough. The term "body lumen" as used herein, means an inner open space of cavity of a tubular organ, such as a blood vessel, intestine, or esophagus. The term "proximal" as used herein means portion of the device which is closer to the user, while the term "distal" refers to a portion of the device which is further from the user.

Figure 1A:
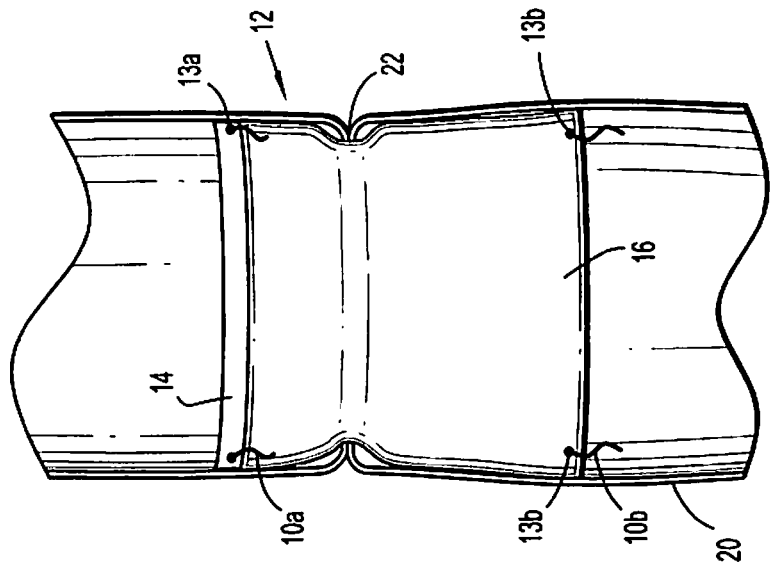
FIG. 1A is a cross-sectional view of a sheath in a compressed position, with a retention member intact.

FIG. 1 illustrates a cross-sectional view of a sheath 12 positioned in a body lumen 20, proximal of an anastomotic site 22. A proximal portion of the sheath 12 includes a ring member 14 and a distal portion of the sheath includes a sleeve 16, which is subsequently elongated distally past an anastomotic site 22. The sheath 12 is held in a compressed position by a retention member 10. The retention member 10 is an elongate polymeric member, e.g. a suture, which is positioned on an interior surface of the sheath 12. Alternately, the retention member 10 may be positioned exterior of the sheath 12. A first portion of the retention member 10a is connected to the ring member 14 at a first connection point 13a, and a second portion of the retention member 10b is connected to the sleeve 16 at a second connection point 13, the second connection point 13b being distal to the first connection point 13a. The retention member 10 may be connected to the sheath 12 at least two connection points (13a, 13b) which enable to sheath be retained in a compressed position. For example, a first connection point may be located at a proximal portion of the sheath and a second connection point may be located at a distal portion of the sheath. At least one retention member 10 (two are shown) may be used to retain the sheath 12 in a first, compressed position for insertion. It is also envisioned that more than two retention members 10 may be used to retain the sheath 12 in a compressed position. Additionally, the retention member 10 may include more than two connection points (13a, 13b), which may enable a more uniform compression of the sheath 12. The retention member 10 may be connected to the sheath 12 using any method within the purview of those skilled in the art including, but not limited to welding, tacking or gluing.

Figure 1B:
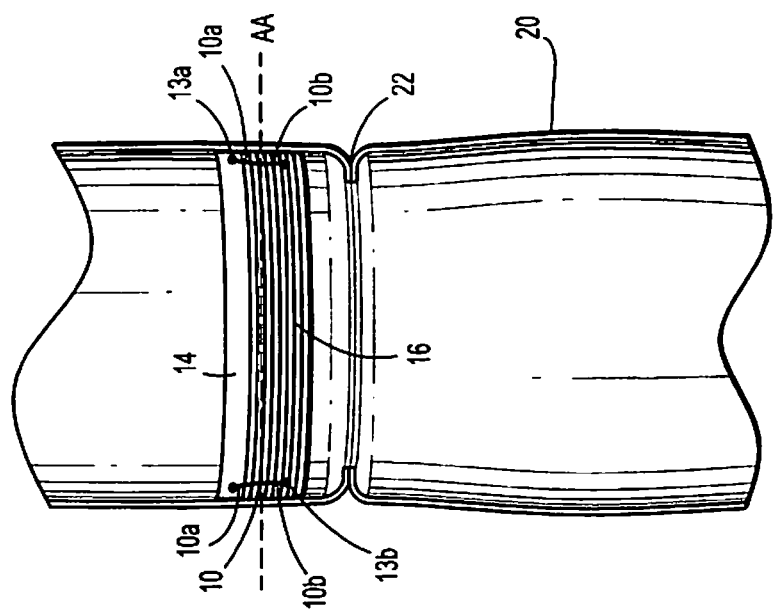
FIG. 1B is a cross-sectional view of the sheath of FIG. 1 in an expanded position, after the retention member of FIG. 1A has been severed.

The sheath 12 may be inserted into a body lumen 20 in a first compressed position, through use of an insertion device (not shown). Once inserted and positioned in a body lumen 20 proximal to an anastomotic site 22, the retention member 10 may be severed, for example, along line A-A, releasing the sheath 12 from a compressed position (FIG. 1B). The sheath 12 may then self expand or elongate distally past an anastomosis 22. Alternately, a separate device, such as a grasper (not shown), may be used to extend a length of the sleeve 16 distally past an anastomotic site.

Figure 2A:
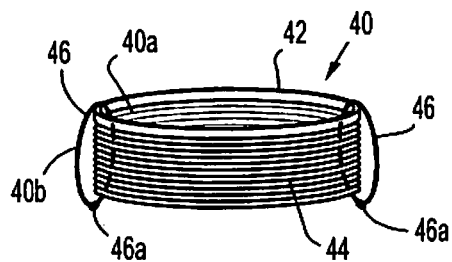
FIGS. 2A-2D are side views of different embodiments of sheath retention members according to the present disclosure.

Various alternate embodiments of retention members are illustrated in FIGS. 2A-2D. FIG. 2A shows a sheath 40 in a compressed position. The sheath 40 includes a ring member 42 and a sleeve 44, the sleeve 44 extending distally from the ring member 42. The ring member 42 is generally rigid so as to maintain the sheath 40 in a fixed position in situ, applying radial pressure to a body lumen. The sheath 40 is retained in a compressed position by a retention member 46, as shown in FIG. 2A. The retention member 46 is a suture which is wrapped around an inner portion 40a and an outer portion 40b of the sheath and ends of the suture 46 are fastened or knotted together at 46a, creating a closed loop around the sheath 40. FIG. 2A shows two retention members 46 positioned about 180 degrees apart, so as to uniformly confine the sheath 40 to a shorter length at least for insertion. The retention members 46 may be moveably (i.e. slideably) positioned on the sheath 40 (as shown). Alternately, the retention members 46 may be positioned at a fixed location or series of locations along the circumference of the sheath 40. It is also contemplated that more than two retention members 46 may be used to confine the sheath 40 to a shorter length. Once the sheath 40 is positioned in a body lumen, a user may sever and optionally remove the retention members 46. The sheath 40 may then be elongated distally past an anastomotic site, enabling fluids to bypass the anastomotic site and protecting the anastomotic site throughout the wound healing cycle. It should also be understood that although the illustrated sheaths have a ring member, various embodiments of sheaths, with or without ring members, may be used in combination with the retention members of the present disclosure.

Figure 2B:
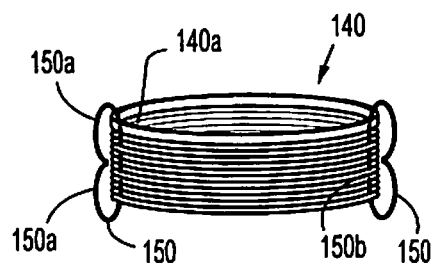
Figure 2C:
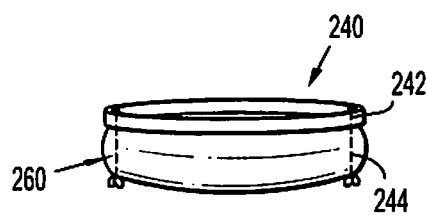
Figure 2D:
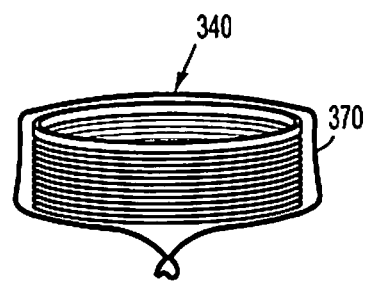

The sheaths shown in FIGS. 2B-2D are similar, with various embodiments of retention members. FIG. 2B illustrates retention members 150 being formed surgical staples having a generally "B"-shaped geometry. The retention members 150 have at least two legs (150a) which are connected therebetween by a backspan 150b. It should be noted that although the legs of the staples (150a, 150b) overlap exterior to the sheath, the legs of the staples (150a) may overlap on the interior portion 140a of the sheath 140, with the backspan 150b positioned exterior to the sheath 140. Two retention members 150 are shown positioned approximately 180 degrees apart so as to uniformly compress the sheath 140. It is contemplated that more than two retention members 150 may be used to retain the sheath 140 in a compressed position. The retention members 150 may be positioned at a fixed location or series of locations along the circumference of the sheath 140 (as shown). Alternately, the retention members 150 may be slideably positioned on the sheath 140. In one embodiment, the retention members 150 may be shape memory polymeric or metallic surgical staples, which once positioned in situ, the retention members 150 may self expand upon reaching body temperature, releasing the sheath 140 from a compressed position and enabling the sheath 140 to longitudinally extend to a second position (not shown). The retention members 150 may be removed from the body once the sheath 140 has been released.

Figure 3B:
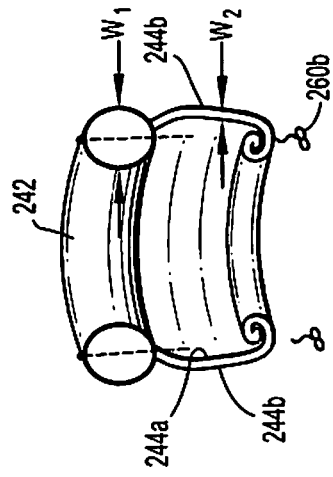
FIG. 3A is a cross-sectional perspective view of the device of FIG. 2C in a first compressed position, with the retention member intact; and, FIG. 3B is another cross-sectional perspective view of the device of FIG. 2C after the retention member has been severed.
Figure 3A:
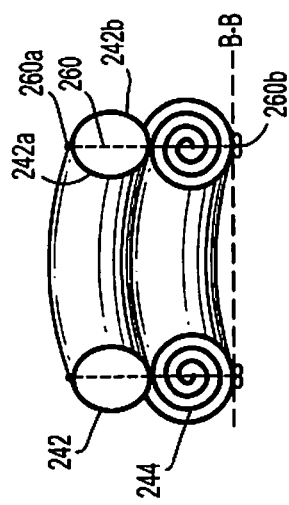

Alternatively, the retention members may be pins or strings which pierce at least a portion of the sheath. FIG. 2C illustrates the sheath 240 in which the sleeve 244 is rolled proximally, towards the ring member 242. FIG. 3A illustrates a cross-sectional view of the sheath 240 (of FIG. 2C), including a retention member 260 which defines an elongate body, such as a pin or a suture, penetrating at least a portion of the sheath 240. More specifically, the sleeve 244 defines an outer wall 244b and inner wall 244a, the distance between which defines a wall thickness w2. The ring member 242 also has a wall thickness w1, which is the diameter of the ring member 242, the ring member 242 being circular in cross-sectional area. The retention member 260 penetrates at least a portion of the sleeve and the ring member.

The retention member 260 includes at least two ends, a first end of the retention member 260 penetrates the wall thickness w2 of the sleeve 240, and a second end of the retention member 260 penetrates at least a portion of the wall thickness w1 of the ring member 242. Alternatively, the retention member 260 may only penetrate the sleeve 244. The elongate body 260 runs through the walls of the sleeve 244 and ring member 242, connecting the first end to the second end. As shown, the retention member penetrates the sheath 240 along a centerline. The ends of the retention member 260 may include a portion which is tacked or welded at 260a to the sleeve 244. Alternatively, at least one end 260b of the retention member 260 may be secured to the sheath 240 by piercing the sheath wall and knotting or tying the ends of the retention member 260. The retention member 260 retains the sheath 240 in a compressed position and the two ends of the elongate body 260 prevent the sheath from unraveling. When at least one end of the retention member is severed (FIG. 3B), the sheath 240 may be elongated distally past an anastomotic site. It should be noted that although the retention member 260 penetrates both sleeve 244 and the ring member 242, the retention member 260 may penetrate the sheath 240 at any point or series of points, which enables the sheath 240 to be restricted in a compressed position.

In another embodiment, a retention member 370 may encapsulate at least a portion of the sheath 340. For example, as shown in FIG. 20, the retention member 370 may be similar to a balloon or a net, surrounding or encapsulating the entire sheath 340, maintaining the sheath 340 in a compressed position. The retention member 370 may be severed or pierced and the retention member 370 may be removed in situ, allowing the sheath to expand to a second, longer length. In some embodiments, the retention member 370 may comprise a water soluble material, e.g. gelatin or cellulose, wherein the retention member 370 may dissolve upon contact with fluids and the sheath 340 can be longitudinally extended past an anastomotic site.

In alternate embodiments, retention members may include polymeric materials which, for example, upon drying, would assist in maintaining the sheath in a compressed state. For example, certain polymeric materials, including polymer solutions, may be processed with the sheath. The sheath may be folded, rolled, or crimped into a compressed position. The sheath may then be dried in an oven or at ambient temperature and upon evaporation of the polymer solution, the dried polymer coating (retention member), retains the sheath in a shorter, compressed position. Upon implantation into tissue, the retention member may wet or hydrate, allowing the sheath to expand into a second, longer position. Suitable polymeric materials include but are not limited to those listed below including polysaccharides such as starch, alginate or chitosan and water soluble adhesives. Suitable water soluble adhesives include succinimide-based PEG esters, photocurable vinyl adhesives and aldehydes.

Retention members may comprise both absorbable and non absorbable materials, which may be synthetic or natural materials. Suitable synthetic absorbable materials include polymers such as those made from lactide, glycolide, caprolactone, valerolactone, carbonates (e.g., trimethylene carbonate, tetramethylene carbonate, and the like), dioxanones (e.g., 1,4-dioxanone) i5-valerolactone, 1,dioxepanones (e.g., 1,4-dioxepan-2-one and 1,5-dioxepan-2-one), ethylene glycol, ethylene oxide, esteramides, y-hydroxyvalerate, -hydroxypropionate, alpha-hydroxy acid, hydroxybuterates, orthoesters, hydroxy alkanoates, tyrosine carbonates, polyimide carbonates, polyimino carbonates such as poly (bisphenol A-iminocarbonate) and poly (hydroquinone-iminocarbonate), and polymer drugs (e.g., polydiflunisol, polyaspirin, and protein therapeutics) and copolymers and combinations thereof. Suitable natural absorbable polymers include, fibrin, proteins (e.g. albumin, collagen, gelatin, casein, lactoferrin), and gut and combinations thereof. Additionally, polysaccharides may also be used to as retention members, including agarose, cellulose, carboxymethyl cellulose, methyl cellulose, dextran (e.g. carboxylated dextran, aminated dextran, sulfonated dextran), alginates, chitosan, hyaluronic acid, and fucans. Synthetic polymers and natural polymers may also be combined to make retention members of the enclosed disclosure.

Suitable non-absorbable materials which may be used to form the retention member include non-absorbable natural materials such as cotton, silk, and rubber. Suitable non-absorbable synthetic materials include monomers and polymers derived from materials such as nylons, polyolefins such as polypropylene and polyethylene, ultra high molecular weight polyethylene (UHMWPE), polyamides, polyesters such as poly ethylene terepththalate (PET), polyaryletherketone, polyvinylidene difluoride (PVDF), acrylics such as poly acrylic acid, aramids, fluoropolymers, polybutesters, silicones, and polymer blends, copolymers thereof and combinations with degradable polymers. Hydrophilic vinyl polymers and copolymers such as acrylic acid, polyvinylpyrrolidone, methacrylic acid, potassium sulfopropyl acrylates, bisacrylates, methacrylates including hydroxyethyl methacrylate (HEMA), methacryloyloxyethyl phosphorylcholine (MPC), acrylamide, polypyrrole, vinyl acetate, styrene sulfonic, and hydroxyamates may also be employed as suitable materials for retention members. Combinations and copolymers of various non-absorbable materials may also be used as retention members. Additionally, non-absorbable synthetic and natural polymers and monomers may be combined with each other and may also be combined with various absorbable polymers and monomers to create the retention member.

In other embodiments, the retention member may be constructed using shape memory materials. A thermal shape memory material may be used in certain described embodiments, such as the staple-shaped retention member, where upon temperature activation of a material, the retention member opens and releases a portion of the sheath, allowing it to elongate. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

Absorbable metallic materials may also be used to construct retention members. Suitable absorbable metals and metal alloys include magnesium-based and iron-based alloys. The magnesium-based alloys may additionally include about 1 to 10 wt. % scandium, up to about 3 wt. % yttrium, about 1 to 3 wt. % rare earth metal, and about 0.1 to 0.5 wt. % zirconium.

It should be noted that the present disclosure is not limited to use with specific sheaths for use with colonic and intestinal anastomoses and contemplates retaining other sheath embodiments. Additionally, the above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:
1. A method of treating a patient, comprising the steps of:
positioning a sheath within a body lumen, the sheath defining a longitudinal axis, and being adapted to transition in situ from a first condition having a first longitudinal length to a second condition having a second, greater longitudinal length, the sheath including a retention member comprising a shape memory material and dimensioned to extend between first and second sheath end portions of the sheath to assist in retaining the sheath in the first condition;
advancing the sheath, in the first condition, within the body lumen to a location adjacent an anastomotic site; and
transitioning the sheath from the first condition to the second condition by thermally activating the retention member whereby the retention member releases at least one of the first and second sheath end portions such that the sheath extends across the anastomotic site to thereby assist in healing thereof.

* * * * *